(12) United States Patent
Woo et al.

(10) Patent No.: US 6,605,373 B2
(45) Date of Patent: *Aug. 12, 2003

(54) FLUORENE-CONTAINING POLYMERS AND ELECTROLUMINESCENT DEVICES THEREFROM

(75) Inventors: Edmund P. Woo, Midland, MI (US); Mark T. Bernius, Midland, MI (US); Michael Inbasekaran, Midland, MI (US); Weishi Wu, Midland, MI (US)

(73) Assignee: Dow Global Technologies Inc., Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/808,788

(22) Filed: Mar. 15, 2001

(65) Prior Publication Data

US 2001/0026878 A1 Oct. 4, 2001

Related U.S. Application Data

(63) Continuation of application No. 09/063,615, filed on Apr. 21, 1998, now Pat. No. 6,309,763, which is a continuation-in-part of application No. 08/861,469, filed on May 21, 1997, now Pat. No. 6,169,163.

(51) Int. Cl.[7] .............................................. H05B 33/12

(52) U.S. Cl. ....................... 428/690; 428/917; 428/704; 313/504; 257/40; 257/94

(58) Field of Search ................................ 428/690, 704, 428/917; 313/504; 257/40, 94

(56) References Cited

U.S. PATENT DOCUMENTS

| | | | |
|---|---|---|---|
| 3,641,115 A | 2/1972 | Peck et al. | 60/475 |
| 4,769,292 A | 9/1988 | Tang et al. | 428/690 |
| 5,247,190 A | 9/1993 | Friend et al. | 257/40 |
| 5,399,502 A | 3/1995 | Friend et al. | 437/1 |
| 5,621,131 A | 4/1997 | Kreuder et al. | 558/46 |

(List continued on next page.)

FOREIGN PATENT DOCUMENTS

| | | |
|---|---|---|
| EP | 0707020 A2 | 10/1995 |
| FR | 2702870 | 9/1994 |
| WO | WO 95/01871 | 1/1995 |
| WO | WO 97/05104 | 2/1997 |
| WO | WO 97/33193 | 9/1997 |
| WO | WO 97/39045 | 10/1997 |
| WO | WO 97/46052 | 12/1997 |

OTHER PUBLICATIONS

*Chemical Abstracts*, vol. 126, No. 24, pp. 1142, paragraphs 322719, 322721, 322723 (1997), [no month].

(List continued on next page.)

*Primary Examiner*—Marie Yamnitzky

(57) ABSTRACT

A copolymer comprising 10–90 percent by weight of groups of Formula (I):

(I)

and from 10–90 percent by weight of groups selected from Formulas (II), (III), and (IV):

(II)

(III)

and (IV)

and mixtures thereof; wherein $R^1$ is independently in each occurrence H, $C_1$–$C_{20}$ hydrocarbyl or $C_1$–$C_{20}$ hydrocarbyl containing one or more S, N, O, P or Si atoms, $C_4$–$C_{16}$ hydrocarbyl carbonyloxy, $C_4$–$C_{16}$ aryl(trialkylsiloxy) or both $R^1$ may form with the 9-carbon on the fluorene ring a $C_5$–$C_{20}$ cycloaliphatic structure or a $C_4$–$C_{20}$ cycloaliphatic structure containing one or more heteroatoms of S, N, or O; $R^2$ is independently in each occurrence $C_1$–$C_{20}$ hydrocarbyl, $C_1$–$C_{20}$ hydrocarbyloxy, $C_1$–$C_{20}$ thioether, $C_1$–$C_{20}$ hydrocarbylcarbonyloxy or cyano; $R^3$ is independently in each occurrence carboxyl, $C_1$–$C_{20}$ alkyl, $C_1$–$C_{20}$ alkoxy or a group of the formula —$CO_2R^4$ wherein $R^4$ is a $C_1$–$C_{20}$ alkyl; and a and b are independently in each occurrence an integer from 0 to 3.

2 Claims, No Drawings

U.S. PATENT DOCUMENTS

| | | | | |
|---|---|---|---|---|
| 5,679,760 | A | 10/1997 | Mullen et al. | 528/220 |
| 5,682,043 | A | 10/1997 | Pei et al. | 257/40 |
| 5,708,130 | A | 1/1998 | Woo et al. | 528/397 |
| 5,728,801 | A | 3/1998 | Wu et al. | 528/422 |
| 5,777,070 | A | 7/1998 | Inbasekaran et al. | 528/394 |
| 5,814,244 | A | 9/1998 | Kreuder et al. | 252/301.16 |
| 5,858,563 | A | 1/1999 | Sano et al. | 428/690 |
| 5,879,821 | A | 3/1999 | Hsieh | 428/690 |
| 5,929,194 | A | 7/1999 | Woo et al. | 528/229 |
| 5,998,045 | A | 12/1999 | Chen et al. | 428/690 |
| 6,309,763 | B1 * | 10/2001 | Woo et al. | 428/690 |

OTHER PUBLICATIONS

Burrows, et al., *Applied Physics Letters*, vol. 64, No. 20, pp. 2718–2720 (May 16, 1994).
*Chemical Abstracts*, vol. 126, No. 24, pp. 1142, paragraphs 322719, 322719, 322721, 322723 (1997), [no month].
Cho, et al., *Advanced Materials*, vol. 9, No. 4, pp. 326–328 (1997), [no month].
Cho, et al., *Macromol, Symp.*, vol. 125, pp. 133–142 (1997), [no month].
Colon, et al., *Journal of Organic Chemistry*, vol. 51, pp. 2627–2637 (1986), [no month].
Colon, et al., *Journal of Polymer Science, Part A. Polymer Chemistry*, vol. 28, pp. 367–383 (1990), [no month].
Fujii, et al., *Japanese Journal of Applied Physics*, vol. 34, No. 4B, pp. L499–L502 (Apr. 15, 1995).
Fukuda, et al., *Japanese Journal of Applied Physics*, vol. 28, No. 8, pp. L1433–L1435 (Aug. 1989).
Fukuda, et al., *Journal of Polymer Science: Part A: Polymer Chemistry*, vol. 31, pp. 2465–2471 (1993), [no month].
Hamada, et al., *Chemistry Letters*, pp. 905–906 (1993), [no month].
Hamada, et al., *Optoelectronics–Devices and Technologies*, vol. 7, No. 1, pp. 83–93 (Jun. 1992).
Ioyda, et al., *Bulletin of the Chemical Society of Japan*, vol. 63, pp. 80–87 (1990), [no month].
Kido, et al., *Chemistry Letters*, pp. 47–48 (1996), [no month].
Kim, et al., *Polym. Prepr.*, vol. 38, No. 1, pp. 417–418 (1997), [no month].
Larmat, et al., *American Chemical Society Polymer Reprint*, pp. 799–800 (Mar. 4, 1996).
Le Deit, et al., *Synthetic Metals*, vol. 47, pp. 373–376 (1992), [no month].

Li, et al., *Journal of the Chemical Society, Chemical Communication*, pp. 2211–2212 (1995), [no month].
Miyaura, et al., *Chemical Reviews*, vol. 95, pp. 2457–2483 (1995), [no month].
Miyaura, et al., *Synthetic Communications*, vol. 11, No. 7, pp. 513–519 (1981), [no month].
O'Brien, et al., *Synthetic Metals*, vol. 76, pp. 105–108 (1996), [no month].
Ohmori, et al., *Japanese Journal of Applied Physics*, vol. 30, No. 11B, pp. L1941–L1943 (Nov. 1991).
Ohmori, et al., *Japanese Journal of Applied Physics*, vol. 32, No. 11B, pp. L1663–L1666 (Nov. 15, 1993).
Ohmori, et al., *Journal of Physics D: Applied Physics*, vol. 29, pp. 2983–2987 (1996), [no month].
Pai, et al., *Journal of Physical Chemistry*, vol. 88, No. 20, pp. 4714–4717 (1984), [no month].
Remmers, et al., *Macromolecular Rapid Communications*, vol. 17, pp. 239–252 (1996), [no month].
Sheats, et al., *Science*, vol. 273, pp. 884–888 (Aug. 16, 1996).
Strukelj, et al., *Science*, vol. 267, pp. 1969–1972 (Mar. 31, 1995).
Tang, et al., *Applied Physics Letters*, vol. 51, No. 12, pp. 913–915 (Sep. 21, 1987).
Tang, et al., *Journal of Applied Physics*, vol. 65, No. 9, pp. 3610–3616 (May 1, 1989).
Wallow, et al., *Journal of Organic Chemistry*, vol. 59, pp. 5034–5037 (1994), [no month].
Weaver, et al., *Thin Solid Films*, vol. 273, pp. 39–47 (1996), [no month].
Woo, et al., Meeting of Material Research Society presentation, "Highly Efficient LEDs Based on Fluorene Polymers," (Apr. 13, 1998).
Yamamoto, et al., *Japanese Journal of Applied Physics*, vol. 33, No. 2B, pp. L250–L253 (Feb. 1994).
Yamamoto, *Progress in Polymer Science*, vol. 17 pp. 1153–1205 (1992), [no month].
Yang, et al., *Journal of Applied Physics*, vol. 77, No. 9, pp. 4807–4809 (May 1, 1995).
Yang, et al., *Journal of Applied Physics*, vol. 81, No. 7, pp. 3294–3298 (Apr. 1, 1997).
Yoshida, et al., *Applied Physics Letters*, vol. 69, No. 6, pp. 734–736 (Aug. 5, 1996).

* cited by examiner

FLUORENE-CONTAINING POLYMERS AND ELECTROLUMINESCENT DEVICES THEREFROM

CROSS-REFERENCE TO RELATED APPLICATIONS

This application is a continuation of prior application Ser. No. 09/063,615, filed Apr. 21, 1998, now U.S. Pat. No. 6,309,763 B1; which is a continuation-in-part of Ser. No. 08/861,469, filed May 21, 1997, now U.S. Pat. No. 6,169,163.

BACKGROUND OF THE INVENTION

Polymers containing conjugated groups are known to be useful as materials for preparing organic based light-emitting diodes. However, their light output at low drive voltage and efficiency are less than desirable for certain applications. Thus, there is a need for devices with improved efficiency and a need for devices that can provide high brightness at low drive voltage.

SUMMARY OF THE INVENTION

In one aspect, this invention is a copolymer comprising 10–90 percent by weight of groups of Formula (I):

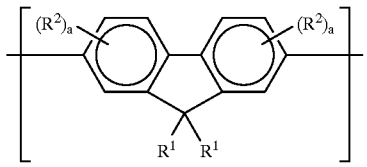

(I)

and from 10–90 percent by weight of groups selected from Formulas (II), (III), and (IV):

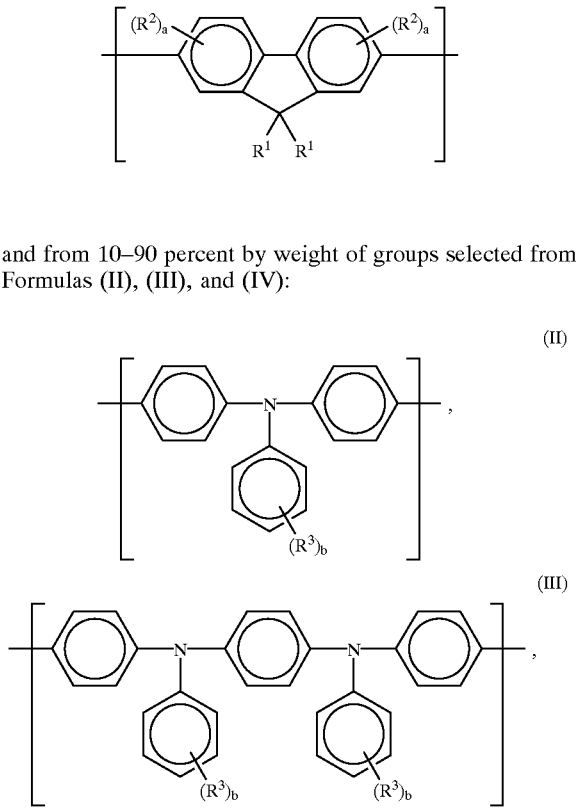

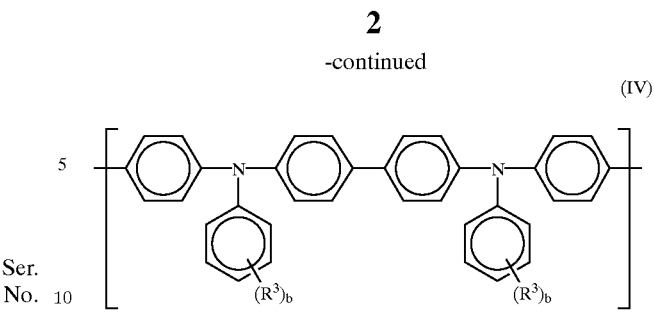

and mixtures thereof; wherein $R^1$ is independently in each occurrence H, $C_1$–$C_{20}$ hydrocarbyl or $C_1$–$C_{20}$ hydrocarbyl containing one or more S, N, O, P or Si atoms, $C_4$–$C_{16}$ hydrocarbyl carbonyloxy, $C_4$–$C_{16}$ aryl(trialkylsiloxy) or both $R^1$ may form with the 9-carbon on the fluorene ring a $C_5$–$C_{20}$ cycloaliphatic structure or a $C_4$–$C_{20}$ cycloaliphatic structure containing one or more heteroatoms of S, N, or O;

$R^2$ is independently in each occurrence $C_1$–$C_{20}$ hydrocarbyl, $C_1$–$C_{20}$ hydrocarbyloxy, $C_1$–$C_{20}$ thioether, $C_1$–$C_{20}$ hydrocarbylcarbonyloxy or cyano;

$R^3$ is independently in each occurrence carboxyl, $C_1$–$C_{20}$ alkyl, $C_1$–$C_{20}$ alkoxy or a group of the formula —$CO_2R^4$ wherein $R^4$ is a $C_1$–$C_{20}$ alkyl; and a and b are independently in each occurrence an integer from 0 to 3.

In a second aspect, this invention is a composition comprising (a) 1–99 percent by weight of the copolymer of the first aspect of the invention, and (b) 99–1 percent by weight of at least one polymer containing groups of Formula (I) and, optionally, conjugated groups other than those of Formulas (II), (III), and (IV).

In a third aspect, this invention is an electroluminescent (EL) device comprising at least one organic film, at least one of which is a light-emitting organic film, arranged between an anode material and a cathode material such that under an applied voltage, holes are injected from the anode material into the organic film adjacent to the anode material and electrons are injected from the cathode material into the organic film adjacent to the cathode material when the device is forward biased, resulting in light emission from the light-emitting organic film; wherein at least one layer comprises the copolymer of the first aspect of the invention.

The copolymers of the invention, when used as a light-emitting and/or hole-transport layer in an electroluminescent device, provide a device with higher efficiency and higher brightness at low drive voltages than a corresponding device without a copolymer of this invention. Efficiency is expressed as lumens/watt (Lm/W). These and other advantages of the invention will be apparent from the description which follows.

DETAILED DESCRIPTION OF THE PREFERRED EMBODIMENTS

The term "conjugated groups" as used herein refers to moieties containing double bonds, triple bonds and/or aromatic rings. The incorporation of such groups into a polymer may be used to modify its light absorption, ionization potential, and/or electronic properties. "Hydrocarbyl" as used herein means any organic moiety containing only hydrogen and carbon unless specified otherwise, and may include aromatic, aliphatic, cycloaliphatic and moieties containing two or more of aliphatic, cycloaliphatic and aromatic moieties.

In the above formulas, $R^1$ is preferably H, $C_1$–$C_{12}$ alkyl, $C_6$–$C_{10}$ aryl or alkyl-substituted aryl, $C_4$–$C_{16}$ hydrocarbylcarbonyloxy, ($C_9$–$C_{16}$ aryl)trialkylsiloxy, a poly(alkyleneoxy) group having a terminal hydroxy, $C_1$–$C_{10}$ hydrocarbyloxy, or a group of the formula: —$(CH_2)_bCO_2R^6$, —$(CH_2)_bSO_3R^6$, —$(CH_2)_bN(R^1)_2$, —$(CH_2)_bN^+(R^1)_3$, or —$(CH_2)_b$—CN, wherein $R^6$ is a $C_1$–$C_6$ hydrocarbyl, H, $Li^+$, $Na^+$, or $K^+$, and b is as defined above. In the embodiment where the two $R^1$ form a ring structure with the 9-carbon atom of the fluorene ring, the ring structure formed is preferably a $C_5$–$C_{20}$ cycloaliphatic structure or a $C_1$–$C_{20}$ cycloaliphatic structure containing one or more heteroatoms of S, N, or O; even more preferably a $C_5$–$C_{10}$ aliphatic ring or a $C_4$–$C_{10}$ aliphatic ring containing one or more of S or O; and most preferably a $C_5$–$C_{10}$ cycloalkyl or $C_4$–$C_{10}$ cycloalkyl containing oxygen.

The fluorene groups in Formula (I) above may further be substituted at the 3-, 4-, 5- or 6-positions with substituents ($R^2$) which do not adversely affect the formation of oligomers or polymers from the corresponding monomers, nor the subsequent processing of the oligomers or polymers for their intended uses. Preferably, $R^2$ is $C_1$–$C_4$ alkoxy, phenoxy, $C_1$–$C_4$ alkyl, phenyl or cyano. However, "a" is preferably 0.

The groups of Formula (I) are preferably present in the copolymer in an amount, based on the weight of the copolymer, of at least 10 percent, more preferably at least 20 percent, most preferably at least 50 percent; but preferably no greater than 99 percent, more preferably no greater than 85 percent, and most preferably no greater than 75 percent. The groups of Formulas (II), (III), and (IV) are preferably present in the copolymer in an amount, based on the weight of the copolymer, of at least 5 percent, more preferably at least 10 percent, most preferably at least 20 percent; but preferably no greater than 95 percent, more preferably no greater than 85 percent, and most preferably no greater than 75 percent.

The polymers and blends of the invention demonstrate strong photoluminescence in dilute solutions or in the solid state. When such materials are exposed to a light of a wavelength of 300–700 nanometers (nm), the materials emit light of wavelengths in the region of 400–800 nm. More preferably, such materials absorb light of wavelengths of from 350–400 nm and emit light of wavelengths in the region of 400–650 nm. The polymers and blends of the invention are readily soluble in common organic solvents. They are processible into thin films or coatings by conventional techniques.

The fluorene oligomers or polymers of this invention preferably have a weight average molecular weight of 1000 Daltons or greater, more preferably 5000 Daltons or greater, even more preferably 10,000 Daltons or greater, even more preferably 15,000 Daltons or greater and most preferably 20,000 Daltons or greater; preferably 1,000,000 Daltons or less, more preferably 500,000 Daltons or less and most preferably 200,000 Daltons or less. Molecular weights are determined according to gel permeation chromatography using polystyrene standards. The degree of polymerization of the polymers of the invention is preferably at least 3.

Preferably, the copolymers of the invention demonstrate a polydispersity (Mw/Mn) of 5 or less, more preferably 4 or less, even more preferably 3 or less, even more preferably 2.5 or less and most preferably 2.0 or less.

Preferably, the copolymer of the first aspect of the invention has one of the following structures:

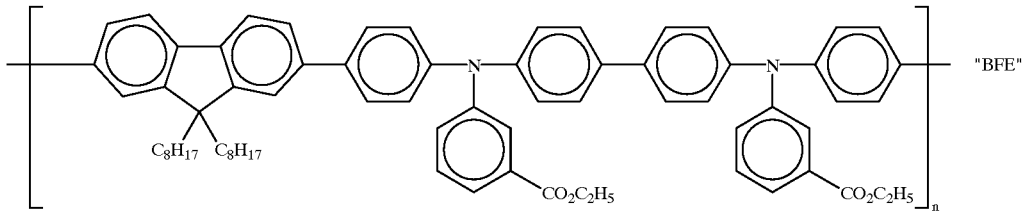

(V) "BFE"

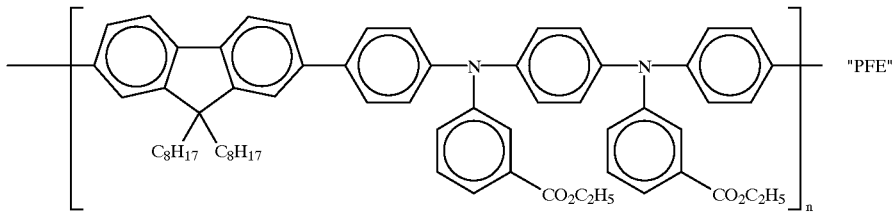

(VI) "PFE"

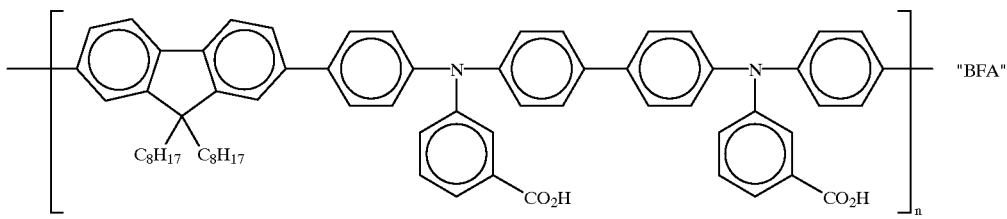

(VII) "BFA"

-continued

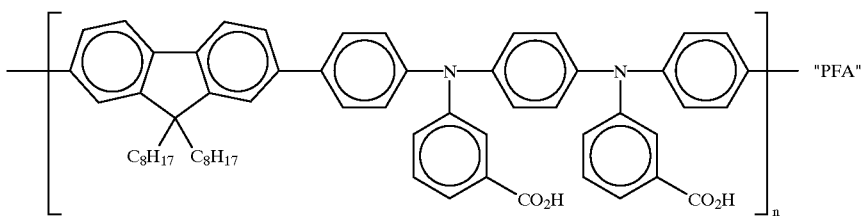
(VIII) "PFA"

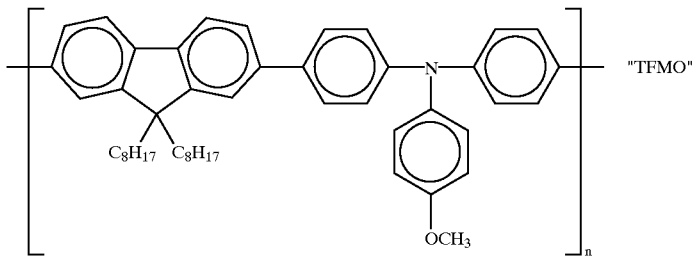
(IX) "TFMO"

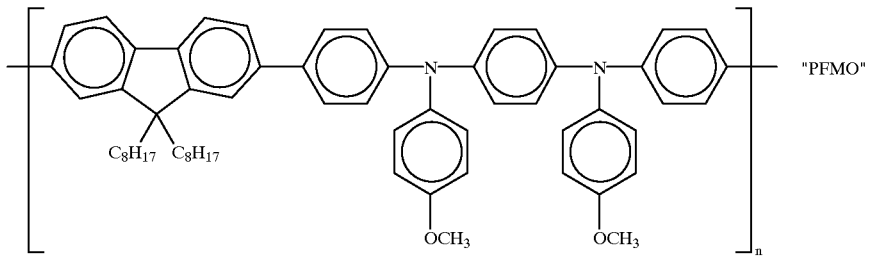
(X) "PFMO"

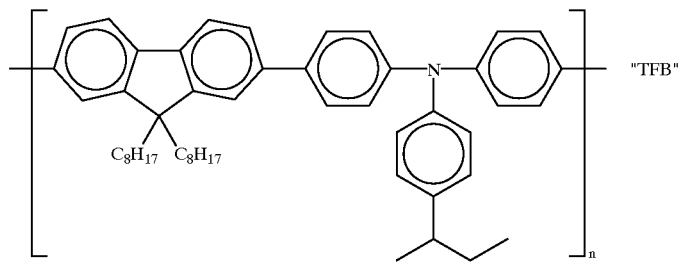
(XI) "TFB"

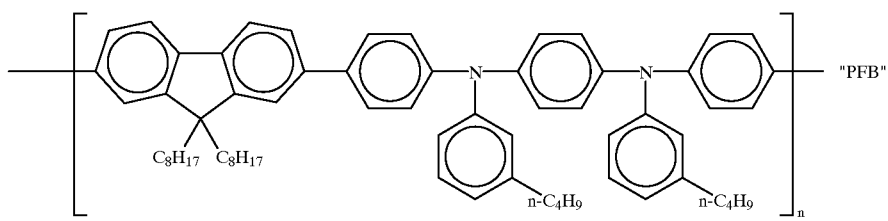
(XII) "PFB"

wherein n is a number greater than 3.

Processes for Preparing Polymers

The polymers containing groups of Formulas (I)–(IV) may be prepared by any suitable process, but are preferably prepared by one of the processes described below. The condensation reaction of an aromatic boronate and a bromide, commonly referred to as the "Suzuki reaction", is described in N. Miyaua and A. Suzuki, *Chemical Reviews*, Vol. 95, pp. 457–2483 (1995). This reaction can be applied to prepare high molecular weight polymers and copolymers.

To prepare polymers, a dibromide having an internal group selected from Formulas (I)–(IV), or mixtures thereof, is reacted with an equimolar amount of diboronic acid or diboronate having an internal group selected from Formulas (I)–(IV), or mixtures thereof, under the catalytic action of Pd and triphenylphosphine. The reaction is typically conducted at about 70° C. to 120° C. in an aromatic hydrocarbon solvent such as toluene. Other solvents such as dimethylformamide and tetrahydrofuran can also be used alone, or in mixtures with, an aromatic hydrocarbon. An aqueous base, preferably sodium carbonate or bicarbonate, is used as the HBr scavenger. Depending on the reactivities of the reactants, a polymerization reaction may take 2 to 100 hours. Other variations of reaction conditions are given in T. I. Wallow and B. M. Novak, *Journal of Organic Chemistry*, Vol. 59, pp. 5034–5037 (1994); in M. Remmers, M. Schulze, and G. Wegner, *Macromolecular Rapid Communications*, Vol. 17, pp. 239–252 (1996); and in pending U.S. application Ser. No. 08/956,797 filed Oct. 23, 1997, now U.S. Pat. No. 5,777,070 which is hereby incorporated by reference in its entirety. An alternating copolymer results when a dibromide having one type of internal group selected from Formulas (I)–(IV) is reacted with a boron-containing monomer having a different internal group selected from Formulas (I)–(IV). If desired, a monofunctional aryl halide or aryl boronate may be used as a chain-terminator in such reactions, which will result in the formation of a terminal aryl group. For the purpose of preparing high molecular weight polymers, more than one diboronic acid/diboronate and more than one dibromide may be used in a Suzuki polymerization reaction so long as the total molar amount of diboronic acids/diboronates is essentially equivalent to the total amount of dibromides.

It is possible to control the sequencing of the monomeric units in the resulting copolymer by controlling the order and composition of monomer feeds in the Suzuki reaction. For instance, a high molecular weight copolymer comprising mainly large blocks of fluorene homopolymers connected to short blocks of alternating fluorene-comonomer oligomers may be made by first introducing into the reaction reactants in the appropriate ratio to make the alternating fluorene-comonomer oligomers followed by the remainder of fluorene monomers so long as there is an overall balance of boronic and bromo groups.

An alternative polymerization process involves only dihalo-functional reactants, and may be carried out using nickel coupling reactions. One such coupling reaction is described in Colon et al., *Journal of Polymer Science*, Part A, Polymer Chemistry Edition, Vol. 28, p. 367 (1990), incorporated herein by reference, and in Colon et al., *Journal of Organic Chemistry*, Vol. 51, p. 2627 (1986). The reaction is typically conducted in a polar aprotic solvent (e.g., dimethylacetamide) with a catalytic amount of nickel salt, a substantial amount of triphenylphosphine, and a large excess of zinc dust. A variant of this process is described in Ioyda et al., *Bulletin of the Chemical Society of Japan*, Vol. 63, p. 80 (1990), wherein an organo-soluble iodide was used as an accelerator. Another nickel-coupling reaction is disclosed in Yamamoto, *Progress in Polymer Science*, Vol. 17, p. 1153 (1992), wherein a mixture of dihaloaromatic compounds were treated with an excess amount of nickel (1,5-cyclooctadiene) complex in an inert solvent. All nickel-coupling reactions when applied to reactant mixtures of two or more aromatic dihalides yield essentially random copolymers. Such polymerization reactions may be terminated by the addition of small amounts of water to the polymerization reaction mixture, which will replace the terminal halogen groups with hydrogen groups. Alternatively, a monofunctional aryl halide may be used as a chain-terminator in such reactions, which will result in the formation of a terminal aryl group.

In one embodiment, the polymers of component (b) of the second aspect of the invention contain conjugated groups different from fluorene and amine groups described above. Such polymers may be prepared using the methods described above incorporating at least one conjugated monomeric compound different from the fluorene and amine groups described above.

Examples of conjugated comonomers include stilbene, tolan, $C_6$–$C_{20}$ mononuclear/polynuclear aromatic hydrocarbons, and $C_2$–$C_{10}$ mononuclear/polynuclear heterocycles.

Examples of mononuclear/polynuclear aromatic hydrocarbons include benzene, naphthalene, acenaphthene, phenanthrene, anthracene, fluoranthene, pyrene, rubrene, and chrysene. Examples of mononuclear/polynuclear heterocycles include 5-member heterocycles such as furan, thiophene, pyrrole, oxazole, isooxazole, thiazole, isothiazole, imidazole, oxadiazoles, thiadiazole, and pyrazoles; 6-member heterocycles such as pyridine, pyridazine, pyrimidine, pyrazine, triazines, and tetrazenes; benzo-fused ring systems such as benzoxazole, benzothiazole, benzimidazole, quinoline, isoquinoline, cinnoline, quinazoline, quinoxaline, phthalazine, benzothiadiazole, and benzotriazines; and polynuclear condensed ring systems such as phenazine, phenanthridine, acridine, carbazole, and diphenylene oxide. In general, conjugated compounds containing up to 30 carbons are useful for the present purpose. They may be substituted optionally with one or more substituents that are not deleterious to the photoluminescent properties of the polymer compositions. Examples of substituents include $C_1$–$C_{20}$ hydrocarbyl radicals, $C_1$–$C_{20}$ (thio) alkoxy radicals, $C_1$–$C_{20}$ (thio)aryloxy radicals, cyano, fluoro, chloro, $C_1$–$C_{20}$ alkoxycarbonyl, $C_1$–$C_{20}$ aryoxylcarbonyl, $C_1$–$C_{20}$ carboxyl, and alkyl(aryl)sulfonyl radicals. Substituents which are known photoluminescent quenchers, such as arylcarbonyl and nitro, are undesirable.

Conjugated monomeric units of more complex structures, as exemplified by Structures (1)–(8), may also be used.

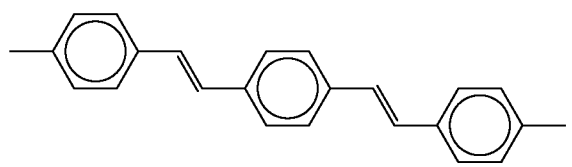

(1)

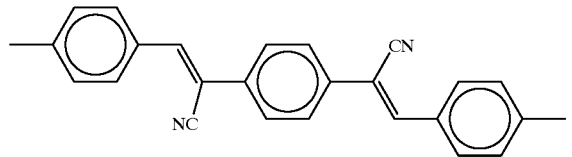

(2)

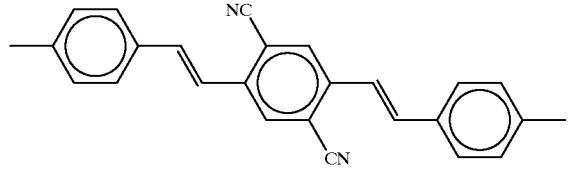

(3)

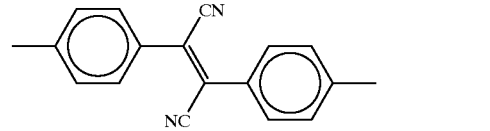

(4)

(5)

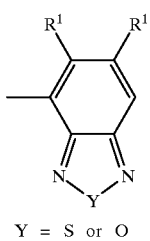

Y = S or O (6)

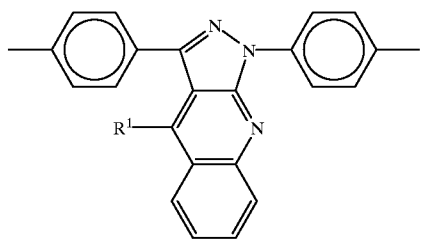

(7)

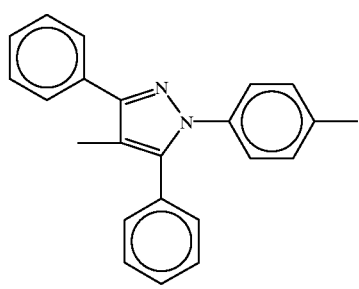

(8)

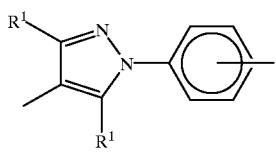

Fluorene-Containing Monomers

Fluorene-containing monomers useful in preparing the polymers of the invention include compounds of the formulas:

(XIII)

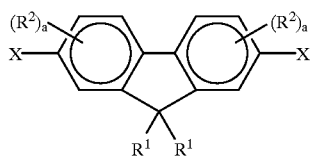

(XIV)

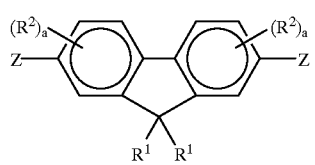

wherein $R^1$, $R^2$, and a are as defined above;
X is independently in each occurrence a halogen moiety; and
Z is independently in each occurrence —$B(OH)_2$, —$B(OR^4)_2$ or

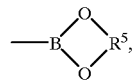

wherein $R^4$ is independently in each occurrence a $C_1$–$C_{10}$ alkyl group and $R^5$ is independently in each occurrence a $C_2$–$C_{10}$ alkylene group.

X is preferably chlorine or bromine; but is most preferably bromine. Z is preferably a cyclic boronate derived from ethylene glycol or propylene glycol.

The boron-containing fluorene compounds may be prepared by any suitable method. An example of reaction conditions for preparing boron-containing compounds is described in Remmers et al., *Macromolecular Rapid Communications*, Vol. 17, pp. 239–253 (1996). Compounds of a corresponding dihalo-functional compound may be converted to the corresponding dilithio derivative by reaction with two equivalents of butyllithium. Reaction of the dilithio derivative with a trialkylborate followed by hydrolysis yields the corresponding diboronic acid ($Z=B(OH)_2$). Esterification of the diboronic acid with an alkylenediol, such as ethylene glycol, gives the di(cyclic)boronate.

Amine-Containing Monomers

The amine-containing monomers for the synthesis of the copolymers of the first aspect of the invention may be prepared according to the procedures disclosed in U.S. Pat. No. 5,728,801, which is hereby incorporated by reference in its entirety.

Polymer Blends

In a second aspect, this invention is a composition comprising (a) 1–99 percent by weight of the copolymer of the first aspect of the invention, and (b) 99–1 percent by weight of at least one polymer containing groups of Formula (I) and, optionally, conjugated groups other than those of Formulas (II), (III), and (IV).

A characteristic of the amine copolymers of the first aspect of the invention is the low barrier to hole injection from the anode into them. Thus, electroluminescent devices comprising at least one of these copolymers usually exhibit lower turn-on voltage than the corresponding devices without it. Incorporation of these copolymers into devices can be accomplished either by constructing multi-layer devices wherein the amine copolymer is deposited as a separate layer, or by constructing single layer devices wherein the amine copolymer is blended with the emitting polymer and the mixture deposited as one layer.

Preferably, component (a) comprises at least 1 percent by weight, more preferably at least 10 percent, most preferably at least 20 percent; but preferably no greater than 99 percent, more preferably no greater than 95 percent, and most preferably no greater than 90 percent, based on the weight of components (a) and (b).

Component (b) of the blend of the invention may be a conjugated homopolymer, or a random, block, or alternating copolymer having a degree of polymerization of at least 3. Preferably, the polymer or copolymer is highly fluorescent and is readily soluble in most common organic solvents. Examples of suitable polymers containing conjugated groups include polyfluorenes, alternating copolymers comprising monomeric unit of Formula (XV):

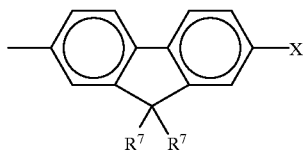 (XV)

where $R^7$ is independently in each occurrence a $C_1$–$C_{12}$ hydrocarbyl group, and other monomeric units selected from Structures (1)–(8).

Polymer Applications

Another aspect of the invention is the films formed from the polymers of the invention. Such films can be used in polymeric light-emitting diodes. Preferably, such films are used as emitting layers or charge carrier transport layers. These polymers may also be used as protective coatings for electronic devices and as fluorescent coatings. The thickness of the coating or film is dependent upon the ultimate use. Generally, such thickness can be from 0.01–200 microns. In that embodiment wherein the coating is used as a fluorescent coating, the coating or film thickness is from 50–200 microns. In that embodiment where the coatings are used as electronic protective layers, the thickness of the coating can be from 5–20 microns. In that embodiment where the coatings are used in a polymeric light-emitting diode, the thickness of the layer formed is 0.05–2 microns. The oligomers or polymers of the invention form good pinhole- and defect-free films. Such films can be prepared by means well known in the art including spin-coating, spray-coating, dip-coating and roller-coating. Such coatings are prepared by a process comprising applying a composition to a substrate and exposing the applied composition to conditions such that a film is formed. The conditions which form a film depend upon the application technique. Preferably, a solution processing method is utilized, using a 0.1–10 weight percent solution of the desired polymers in a common organic solvent. For thin coatings, it is preferred that the film-forming composition contains from 0.5–5.0 percent by weight of the oligomers or polymers. This composition is then applied to the appropriate substrate by the desired method and the solvent is allowed to evaporate. Residual solvent may be removed by vacuum and/or by heat. If the solvent is low boiling, then low solution concentrations, for example, 0.1–2 percent, are desired. If the solvent is high boiling, then high concentrations, for example, 3–10 percent, are desired.

Yet another aspect of the invention relates to organic electroluminescent (EL) devices comprising a film of the polymers of this invention. An organic EL device typically consists of an organic film sandwiched between an anode and a cathode such that when a positive bias is applied to the device, holes are injected into the organic film from the anode, and electrons are injected into the organic film from the cathode. The combination of a hole and an electron may give rise to an exciton which may undergo radiative decay to the ground state by liberating a photon. In practice, the anode is commonly a mixed oxide of tin and indium for its conductivity and transparency. The mixed oxide (ITO) is deposited on a transparent substrate such as glass or plastic so that the light emitted by the organic film may be observed. The organic film may be the composite of several individual layers each designed for a distinct function. Since holes are injected from the anode, the layer next to the anode needs to have the functionality of transporting holes. Similarly, the layer next to the cathode needs to have the functionality of transporting electrons. In many instances, the hole-(electron) transporting layer also acts as the emitting layer. In some instances, one layer can perform the combined functions of hole and electron transport, and light emission. The individual layers of the organic film may be all polymeric in nature or combinations of films of polymers and films of small molecules deposited by thermal evaporation. It is preferred that the total thickness of the organic film be less than 1000 nm. It is more preferred that the total thickness be less than 500 nm. It is most preferred that the total thickness be less than 300 nm. One embodiment of the instant invention is EL devices whose organic film comprises at least one of the polymeric compositions of this invention.

The ITO-glass which serves as the substrate and the anode may be used for coating after the usual cleaning with detergent, organic solvents and UV-ozone treatment. It may also be first coated with a thin layer of a conducting substance to facilitate hole injection. Such substances include copper phthalocyanine, polyaniline and poly(3,4-ethylenedioxy-thiophene) (PEDT); the last two in their conductive forms by doping with a strong organic acid, e.g., poly(styrenesulfonic acid). It is preferred that the thickness of this layer be 200 nm or less; it is more preferred that the thickness be 100 nm or less.

In the cases where a separate hole-transporting layer is used, the polymeric arylamines described in U.S. patent application Ser. No. 08/606,180, filed on Feb. 23, 1996, now abandoned; U.S. patent application Ser. No. 08/696,280, filed on Aug. 13, 1996, now abandoned; and in U.S. Pat. No. 5,728,801, may be used, all of which are hereby incorporated by reference. Other known hole-conducting polymers, such as polyvinylcarbazole, may also be used. The resistance of this layer to erosion by the solution of the copolymer film which is to be applied next is obviously critical to the successful fabrication of multi-layer devices. As the copolymers of this invention are applied as xylene or toluene solutions, the hole-transporting layer needs to be insoluble in these solvents. The thickness of this layer may be 500 nm or less, preferably 300 nm or less, most preferably 150 nm or less. Alternatively, the hole-transporting polymer for these devices may be selected from among semi-conducting polymers such as doped polyaniline, doped poly(3,4-ethylene-dioxythiophene), and doped polypyrrole. By "doping" is meant the blending of a semiconducting polymer (such as emeraldine base of polyaniline and poly(3,4-ethylene-dioxythiophene) with an additive which renders the resulting polymer compositions more conductive. Preferably, the conducting polymer is derived from blending poly(3,4-ethylene-dioxythiophene) with a polymeric acid. More preferably, the polymeric acid contains sulfonic acid groups, and is most preferably poly(styrenesulfonic acid). Most preferred are polymer compositions derived from blending poly(3,4-ethylene-dioxythiophene) with at least two equivalents of poly(styrenesulfonic acid).

In the case where an electron-transporting layer is used, it may be applied either by thermal evaporation of low molecular weight materials or by solution coating of a polymer with a solvent that would not cause significant damage to the underlying film.

Examples of low molecular weight materials include the metal complexes of 8-hydroxyquinoline (as described in Burrows et al., *Applied Physics Letters*, Vol. 64, pp. 2718–2720 (1994)), metallic complexes of 10-hydroxybenzo(h)quinoline (as described in Hamada et al., *Chemistry Letters*, pp. 906–906 (1993)), 1,3,4-oxadiazoles (as described in Hamada et al., Optoelectronics—Devices and Technologies, Vol. 7, pp. 83–93 (1992)), 1,3,4-triazoles (as described in Kido et al., Chemistry Letters, pp. 47–48 (1996)), and dicarboximides of perylene (as described in Yoshida et al., Applied Physics Letters, Vol. 69, pp. 734–736 (1996)).

Polymeric electron-transporting materials are exemplified by 1,3,4-oxadiazole-containing polymers (as described in Li et al., Journal of Chemical Society, pp. 2211–2212 (1995), and in Yang and Pei, Journal of Applied Physics, Vol. 77, pp. 4807–4809 (1995)), 1,3,4-triazole-containing polymers (as described in Strukelj et al., Science, Vol. 267, pp. 1969–1972 (1995)), quinoxaline-containing polymers (as described in Yamamoto et al., Japan Journal of Applied Physics, Vol. 33, pp. L250–L253 (1994), and in O'Brien et al., Synthetic Metals, Vol. 76, pp. 105–108 (1996)), and cyano-PPV (as described in Weaver et al., Thin Solid Films, Vol. 273, pp. 39–47 (1996)). The thickness of this layer may be 500 nm or less, preferably 300 nm or less, most preferably 150 nm or less.

The metallic cathode may be deposited either by thermal evaporation or by sputtering. The thickness of the cathode may be from 100 nm to 10,000 nm. The preferred metals are calcium, magnesium, indium, and aluminum. Alloys of these metals may also be used. Alloys of aluminum containing 1–5 percent of lithium and alloys of magnesium containing at least 80 percent of magnesium are preferred.

The EL devices of this invention emit light when subjected to an applied voltage of 50 volt or less with luminance efficiency of at least 0.1 lumens/watt, but which may be as high as 2.5 lumens/watt.

In a preferred embodiment, the electroluminescent device comprises at least one copolymer of the invention, arranged between an anode material and a cathode material such that under an applied voltage, holes are injected from the anode material into the hole-transporting polymer film and electrons are injected from the cathode material into the light-emitting polymer films when the device is forward biased, resulting in light emission from the light-emitting layer.

The term "anode material" as used herein refers to a semi-transparent, or transparent, conducting film with a work function between 4.5 electron volts (eV) and 5.5 eV. Examples are oxides and mixed oxides of indium and tin, and gold. The term "cathode material" as used herein refers to a conducting film with a work function between 2.5 eV and 4.5 eV. Examples are lithium, calcium, magnesium, indium, silver, aluminum, ytterbium, or blends and alloys of the above.

Illustrative Embodiments

The following examples are included for illustrative purposes only and do not limit the scope of the claims.

The amine copolymers in the examples herein have the structures of Formulas (V)–(XII). The other polymers named in the examples herein have the following structures:

F8

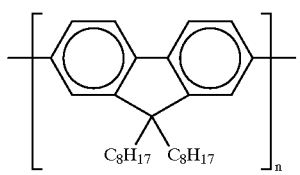

-continued

BT

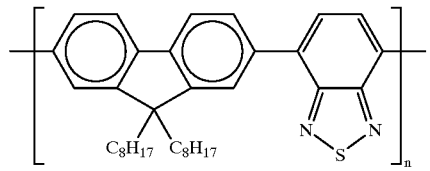

The blends of the second aspect of the invention are prepared by blending an amine copolymer of the first aspect of the invention with F8 or with a mixture of F8 and BT. The notation "3BTF8" represents a blend of 3 weight percent BT in F8; similarly "5BTF8" represents a blend of 5 weight percent BT in F8.

The syntheses of these polymers and their precursor monomers are described in PCT Publication No. WO 97/05184 and copending U.S. patent application Ser. No. 08/956,797, filed on Oct. 23, 1997, now U.S. Pat. No. 5,777,070 entitled "Process for Preparing Conjugated Polymers", both of which are hereby incorporated by reference in their entirety.

EXAMPLE 1

Single-Layer Devices

Single-layer electroluminescent devices are prepared by spin-coating of the appropriate xylene solutions of polymer blends onto ITO-glass, followed by deposition of calcium cathodes. The polymer blend components are 5BTF8 and amine copolymers. Device operational parameters at a brightness of 1000 Cd/M$^2$ are tabulated in Table 1 together with a measure of efficiency, namely, lumens/watt, obtained according to the formula $\pi L/(10 \, JV)$ where L is 1000 Cd/m$^2$. Bias voltage (V) is the voltage at which a brightness of 1000 Cd/m$^2$ is attained; similarly current density (J) is the current per unit area of the device at 1000 Cd/m$^2$, and is given in mA/cm$^2$.

TABLE 1

Single-Layer Devices

| Device | Film thickness (nm) | Amine Copolymer | Ratio* | V | J (mA/cm$^2$) | Lumens/watt |
|---|---|---|---|---|---|---|
| 1a | 150 | none | 0:1 | 16.8 | 39.1 | 0.48 |
| 1b | 100 | TFB | 1:3 | 6.6 | 21.9 | 2.17 |
| 1c | 100 | PFB | 1:3 | 5.6 | 63.4 | 0.88 |
| 1d | 150 | PFMO | 1:3 | 9.3 | 41.6 | 0.81 |
| 1e | 150 | BFE | 1:5 | 10.9 | 47.7 | 0.60 |
| 1f | 150 | BFE | 1:3 | 5.6 | 21.1 | 2.66 |
| 1g | 150 | PFE | 1:3 | 9.3 | 37.5 | 0.90 |

*Ratio of amine copolymer to 5BTF8 by weights.

Device 1a, based on a polymer film without an amine copolymer, required a significantly higher drive voltage than those based on polymer films containing an amine copolymer, to reach a brightness of 1000 Cd/m$^2$. It has the lowest efficiency.

EXAMPLE 2

Double-Layer Devices

Two-layer devices are made by spin-coating the first layer (BFA or PFA) from a polymer solution in N,N-dimethylformamide. The film thus formed is dried in vacuum at 60° C.–90° C. The second layer is formed by spin-coating from a xylene solution of the polymer or polymer blend. Layer 2 in each case is the light-emitting layer.

TABLE 2

Double-Layer Devices

| Device | Layer 1 (nm) | Layer 2 (nm)* | V | J (mA/cm²) | Lumens/watt |
|---|---|---|---|---|---|
| 1a | — | 5BTF8 (150) | 16.8 | 39.1 | 0.48 |
| 2a | BFA (25) | 5BTF8 (100) | 9.3 | 36.5 | 0.93 |
| 2b | PFA (25) | 3BTF8 (100) | 8.4 | 31.8 | 1.17 |
| 2c | BFA (40) | F8 (150) | Max brightness = 120 Cd/m² at 24 volts | | |
| 2d | BFA (60) | 10 wt. % TFMO/90 wt. % F8 (100) | 11 | 174 | 0.16 |

*Numbers in parentheses are film thickness in nanometers.

Comparing the performance of 2a and 2b to that of 1a shows the presence of a layer of an amine copolymer of the invention inbetween ITO and layer 2 (the light-emitting layer) provides a marked reduction in the voltage required to achieve 1000 Cd/m² brightness with the concomitant increase in efficiency. Device 2d has a light-emitting polymer film containing an amine copolymer of the invention while 2c does not. The former reaches 1000 Cd/m² at 11 volts while the latter can only attain 120 Cd/m² at 24 volts. These results clearly demonstrate the benefits of the copolymers of the invention, both as a separate hole-transport layer, and as a blend component of the light-emitting layer.

What is claimed is:

1. An article comprising (a) a transparent substrate having on one surface a transparent or semi-transparent conducting layer, (b) a film comprising a copolymer comprising 10–90 percent by weight of groups of Formula (I):

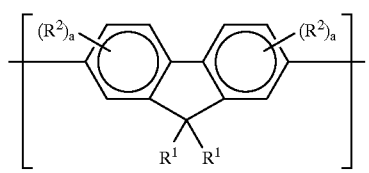

(I)

and from 10–90 percent by weight of groups selected from Formulas (II), (III), and (IV):

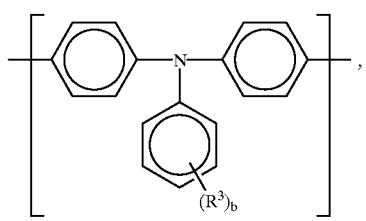

(II)

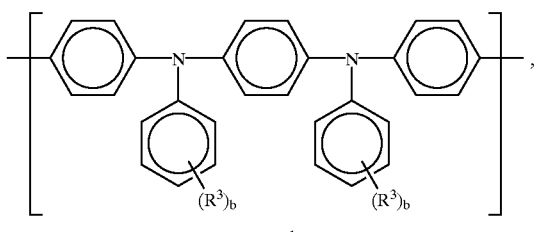

(III)

and

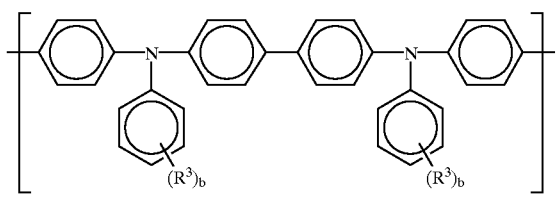

(IV)

and mixtures thereof wherein $R^1$ is independently in each occurrence H, $C_1$–$C_{20}$ hydrocarbyl or $C_1$–$C_{20}$ hydrocarbyl containing one or more S, N, O, P or Si atoms, $C_4$–$C_{16}$ hydrocarbyl carbonyloxy, $C_4$–$C_{16}$ aryl(trialkylsiloxy) or both $R^1$ may form with the 9-carbon on the fluorene ring a $C_5$–$C_{20}$ cycloaliphatic structure or a $C_4$–$C_{20}$ cycloaliphatic structure containing one or more heteroatoms of S, N, or O;

$R^2$ is independently in each occurrence $C_1$–$C_{20}$ hydrocarbyl, $C_1$–$C_{20}$ hydrocarbyloxy, $C_1$–$C_{20}$ thioether, $C_1$–$C_{20}$ hydrocarbylcarbonyloxy or cyano;

$R^3$ is independently in each occurrence carboxyl, $C_1$–$C_{20}$ alkyl, $C_1$–$C_{20}$ alkoxy or a group of the formula —$CO_2R^4$ wherein $R^4$ is a $C_1$–$C_{20}$ alkyl;

a and b are independently in each occurrence 0 or an integer from 0 to 3 and (c) a metallic electrode, wherein the film is located between the transparent or semi-transparent conducting layer and the metallic electrode.

2. The article of claim 1 wherein the film further comprises from 1–99 percent by weight of a second polymer which comprises groups of Formula (I).

* * * * *